United States Patent [19]

Mahawili

[11] Patent Number: 5,336,249
[45] Date of Patent: Aug. 9, 1994

[54] PORTABLE BODY HEATING/COOLING SYSTEM AND METHOD OF USE

[76] Inventor: Imad Mahawili, 1830 Meadow Green Ct., Caledonia, Mich. 49316

[21] Appl. No.: 996,075

[22] Filed: Dec. 23, 1992

Related U.S. Application Data

[63] Continuation-in-part of Ser. No. 893,668, Jun. 5, 1992, abandoned.

[51] Int. Cl.$^5$ .................................................. A61F 7/00
[52] U.S. Cl. ........................................ 607/104; 607/114
[58] Field of Search .......................... 128/394–403; 165/46; 383/901

[56] References Cited

U.S. PATENT DOCUMENTS

| | | | |
|---|---|---|---|
| 2,136,043 | 11/1938 | De Laney | 383/901 |
| 2,706,988 | 4/1955 | Weber | 128/402 |
| 3,894,213 | 7/1975 | Agarwala | 128/402 |
| 3,967,627 | 7/1976 | Brown | 128/400 |
| 4,335,726 | 6/1982 | Kolstedt | 128/400 |
| 4,459,468 | 7/1984 | Bailey | 128/400 |
| 4,523,594 | 6/1985 | Kuznetz | 128/402 |
| 4,662,433 | 5/1987 | Cahn et al. | 128/400 |
| 4,691,762 | 9/1987 | Elker et al. | 128/400 |
| 4,844,072 | 7/1989 | French et al. | 128/400 |
| 4,962,761 | 10/1990 | Golden | 128/400 |

*Primary Examiner*—Mark S. Graham
*Attorney, Agent, or Firm*—John A. Bucher

[57] ABSTRACT

A portable body heating/cooling system and method of use are provided for thermal treatment of selected body portions such as joints, muscles and the like, a reservoir being insulated for containing hot/cold fluid, an elongated and flexible thermal pad having one surface formed by conductive and flexible tubular conduits for conforming to the selected body portion and for producing thermal treatment by the flow of fluid through the tubular conduits, the tubular conduits being connected with the reservoir by non-collapsible supply and return tubes, and a pump preferably battery operated and preferably located in the reservoir for continually circulating fluid from the reservoir through the tubular conduits and back to the reservoir, the thermal pad being equipped with a retainer for securing the thermal pad in contact with the selected body portion, the supply and return tubes preferably being accordion-like in configuration to assure constant circulation of fluid through the thermal pad, the conduit also preferably being corrugated.

11 Claims, 2 Drawing Sheets

PORTABLE BODY HEATING/COOLING SYSTEM AND METHOD OF USE

This is a continuation-in-part of application Ser. No. 07/893,668 filed Jun. 5, 1992, now abandoned.

FIELD OF THE INVENTION

The present invention relates to a system and method of use for heating or cooling selected body portions and more specifically to such a system and method of use wherein a thermal pad is applied to the selected body portion during the treatment.

BACKGROUND OF THE INVENTION

The use of thermal pads for applying hot or cold therapy to different portions of the body has long been recognized as a desirable treatment for a number of conditions. Such treatment has been found helpful in relieving the pain of injuries and arthritis as well as in treating selected body portions such as joints, muscles and the like for sprains, excessive exercise and numerous other conditions.

It is to be noted that the different body portions to be subjected to such treatment include portions of the limbs which can readily be wrapped or encased by a thermal pad as well as substantial, relatively flat portions of the body trunk where the pad must generally be applied in an extended or flat condition.

In treatments of the type summarized above, thermal pads for applying both hot and cold therapy have most commonly relied upon providing a thermal pad which is either hot or cold depending upon the desired treatment. For example, such uses commonly employed heat pads immersed in hot fluid or liquid, electric heat pads, chemical heat pads, cold packs immersed in cold fluid or liquid and direct application of ice to body portions by means of such a thermal pad. These forms of treatment commonly resulted in hot spots, cold spots, cold burns, uncomfortable ice-body contact, moisture on the selected body parts being treated and usually relatively rapid loss of either the hot or cold condition of the pad. Accordingly, it was also necessary to frequently change the pads or to re-immerse them in either hot or cold fluid or liquid.

Improvements in treatment techniques as described above have included the use of improved fasteners such as those available under the VELCRO trade name for securing the pads in place. In addition, although many of the improved systems still employ pads which are themselves either hot or cold, certain prior art systems have been provided for supplying either hot or cold fluid from a separate source. However, these systems were relatively complex. One such system involved the use of an insulated container filled with either hot or cold fluid and connected with heating/cooling units shaped to conform to particular body portions such as the feet or joints. In these prior art systems, fluid from the separate container was allowed to flow to the cuff by gravity and after a selected period of time, the container could be lowered to permit the fluid to flow from the cuff back into the container.

Although these prior art systems and devices were found to be generally adequate for their intended purpose, there has been found to remain a need for further improvements in such systems and methods of use for achieving improved treatment.

SUMMARY OF THE INVENTION

Accordingly, it is an object of the present invention to provide a portable body heating/cooling system and method of use which is adaptable for both hot and cold therapy while also being generally portable to facilitate its use.

More specifically, it is an object of the present invention to provide a portable body heating/cooling apparatus and method of use for thermal heat/cold treatment of selected body portions such as joints, muscles and the like wherein a separate insulated reservoir is provided for containing hot/cold fluid, a thermal pad including conduit means for flow of the fluid therethrough being elongated and flexible with retainer means for applying the pad in extended or flat relation to the body or wrapped around a body joint or limb with the conduit being in conforming and thermally conductive relation with the selected body portion to be treated, non-collapsible supply and return tubes interconnecting the reservoir with the conduit means in the pad, and pump means continually circulating fluid from the reservoir through the conduit means and back to the reservoir to assure a generally uniform temperature in the thermal pad.

In the system and method of use summarized above, the circulation of hot or cold fluid from the reservoir through the thermal pad also serves to achieve a gradual temperature change in the thermal pad which occurs over a relatively short time of seconds but avoids problems such as hot or cold burns developed in the selected body portion when a hot or cold pack is applied directly thereto. Thus, it is a particular advantage of the present invention to provide continual circulation of hot/cold fluid through the thermal pad from a remote source.

More specifically, it is an object of the present invention to locate the pump means within the reservoir and to provide battery operation for the pump means to further enhance portability of the system.

Yet a further object of the invention is to provide the thermal pad with one surface which is substantially formed by the conduit means comprising two parallel tubular conduits formed from a thermally conductive, flexible elastomer for conforming to the selected body portions and for producing thermal treatment by the flow of fluid through the conduits, the tubular conduits being respectively connected at one end to the supply and return tubes and at the other end to each other.

It is a related object of the invention to provide a thermal pad as summarized above and formed from corrugated material in order to limit contact of pad with the selected body portion or portions being treated.

It is a still further object of the invention to provide retainer means for securing the thermal pad in contact with the selected body portion. Such retainer means may preferably comprise fasteners or the like such as those available under the VELCRO trade name as noted above.

Additional objects and advantages of the invention are made apparent in the following description having reference to the accompanying drawings.

DESCRIPTION OF THE PREFERRED EMBODIMENT

Figure 1:
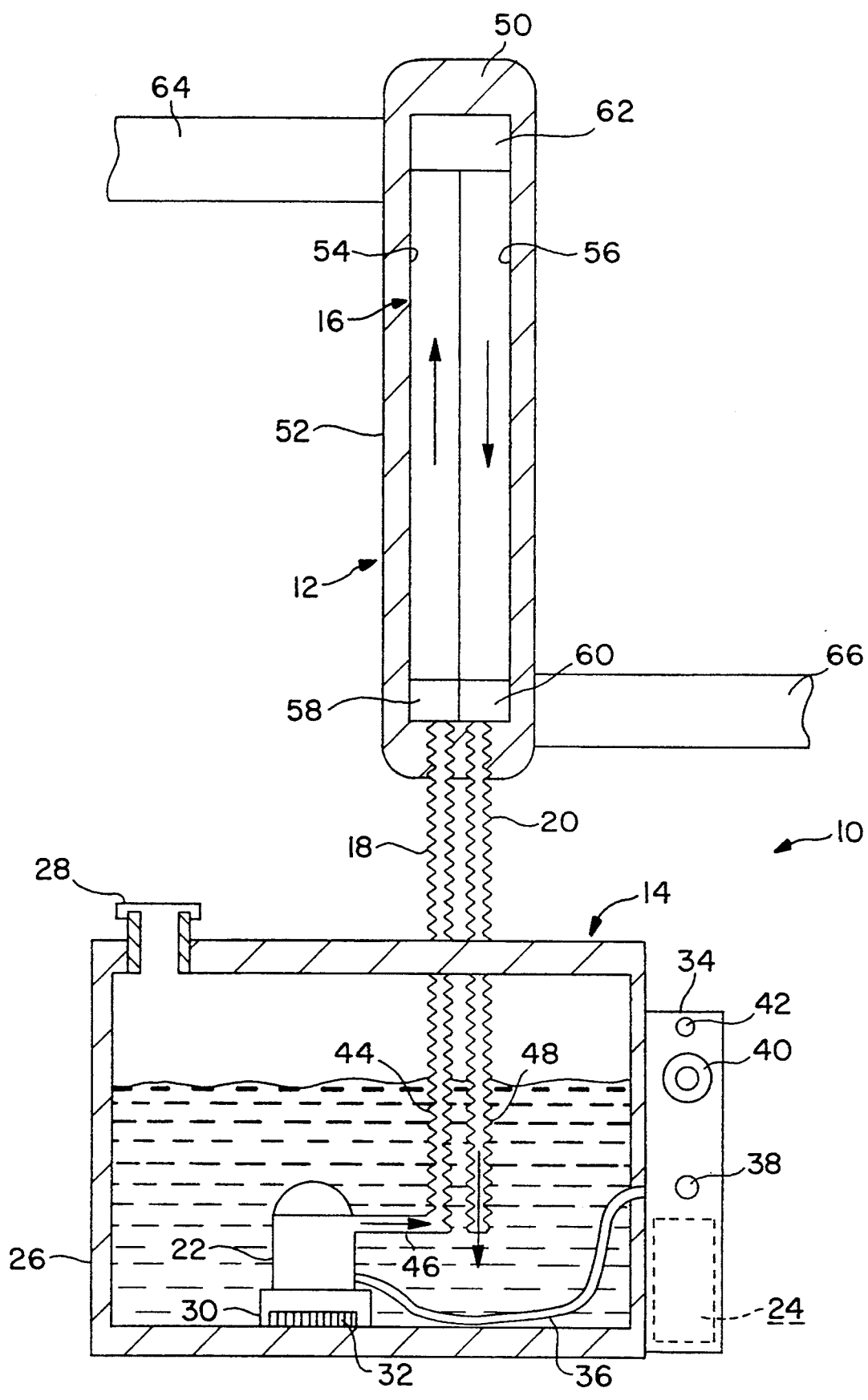
FIG. 1 is a representation of components, partly in section, employed within the portable body heating/cooling system of the present invention and suitable for practicing the method of using the invention.

Referring now to FIG. 1, the present invention provides a portable body heating/cooling apparatus generally indicated at 10 for thermal treatment of selected body portions (not shown) such as joints, muscles and the like. Generally, the portable body heating/cooling apparatus 10 is contemplated to include an elongated, flexible thermal pad novelly configured as described below for conforming to various body portions and for effectively applying hot or cold therapy thereto. A portable reservoir 14 is connected with conduit means 16 in the thermal pad by means of non-collapsible supply and return tubes 18 and 20. A pump 22 is provided for continually circulating fluid from the reservoir through the conduit means and back to the reservoir. The pump 22 is preferably located within the reservoir 14 and operated by a battery 24 in order to further enhance portability and to assure continued circulation of hot/cold fluid through the thermal pad.

The above features of the invention are important both for gradually applying hot or cold therapy to the selected body portion, that is, at least over a period of several seconds during which fluid from the reservoir either heats or cools the conduit means within the thermal pad. Continued circulation of fluid through the thermal pad by means of the pump 22 assures that the thermal pad remains at generally the same desired temperature for the treatment. At the same time, with the fluid being internally circulated through the conduit means 16 by the supply and return tubes 18 and 20, direct contact of the fluid with the body is avoided in order to make the therapy more comfortable to the user.

More specific features of the above components are described below in order to more completely disclose the apparatus and method of use for the invention.

The reservoir 14 is provided with insulated walls 26 in order to maintain the desired temperature of the hot/cold fluid or liquid over extended periods of time. The reservoir is also provided with access means 28 for adding or removing fluid to the reservoir. The pump 22 is preferably of a rotary type as illustrated operated by a submersible DC marine motor 30 of otherwise conventional construction for achieving high volume pumping of the hot or cold fluid or water being circulated through the thermal pad. A grill 32 provides an inlet to the pump 22 to prevent ice from entering and interfering with operation of the pump 22 and motor 30.

The reservoir 14 is preferably provided with an accessory panel 34 containing the battery 24. The battery 24 is connected with the motor 30 by means of a waterproof line 36. A light emitting diode 38 is provided on the panel 34 to indicate when the motor 30 is being operated by the battery 24 under the control of an on-off switch 40.

The reservoir 14 may also be provided with a temperature indicator 42 to indicate the temperature of the fluid or liquid within the reservoir.

The supply and return tubes 18 and 20 are preferably formed with an accordion-like configuration in order to make them non-collapsible and to better assure continued circulation of fluid from the reservoir through the conduit means 16 and back to the reservoir. Within the reservoir, a tubular extension 44 connects the supply tube 18 with an outlet 46 for the pump 22. Similarly, a tubular extension 48 interconnects the return tube to the reservoir, preferably below the level of fluid in the reservoir.

Both the supply and return tubes 18 and 20 as well as their extensions 44 and 48 within the reservoir are preferably formed from polypropylene corrugated tubing which is both light weight and flexible. Preferably, the tubes are all of about 0.5 inch minimum internal diameter in order to minimize back pressure resistance to the high flow marine DC pump 22. Even larger sizes of tubing could accordingly be used for that purpose. However, the specific size of tubing is not a limiting feature of the invention.

The design of the thermal pad 12 is of particular importance to the invention. The thermal pad is illustrated in the figure with one surface 50 being substantially formed by the conduit means 16. The thermal pad 12 includes backing 52 which may be formed from a suitable woven fabric or even an elastomeric material preferably selected to insulate the conduit means 16 and to further enhance comfort of the system to the user. The conduit means 16 is preferably formed with multiple parallel tubular conduits such as those indicated at 54 and 56. The tubular conduits are arranged in parallel so that, when they are flattened against the selected body portion being treated, they substantially fill the surface 50 of the thermal pad 12.

The tubular conduits 54 and 56 have couplings 58 and 60 arranged at one end for respectively interconnecting them with the supply and return tubes 18 and 20. A single coupling 62 serves to interconnect the opposite ends of the tubular conduits 54 and 56 with each other so that fluid from the reservoir may pass from the supply tube 18 into the tubular conduit 54 and then through the tubular conduit 56 to the return tube 20 from which it flow back into the reservoir 14. It is of course apparent that additional tubular conduits could be provided on the surface 50 of the thermal pad to further increase its effective therapy area.

The tubular conduits 54 and 56 are preferably formed from flexible rubber tubes having diameters of at least approximately 1.25 inches or even larger. The use of an elastomer such as rubber is important since it allows the use of the long tubular conduits 53 and 56 to be wrapped about most of the body joints and/or limbs and also to be placed flat against portions of the body, particularly the trunk, such as the back or abdomen. The tubular conduits 54 and 56 are preferably flexible and have the minimum diameter noted above in order to permit fluid flow with minimum back pressure.

Preferably, the pad is substantially elongated and may have dimensions of typically 16 inches in length and about 3 inches in diameter. The width of the pad is selected to assure coverage of the body portion or area being treated. The length of the pad is selected as noted above to enable the pad to be wrapped around the body limbs while also being suitable for arrangement in extended or flat relation on other portions of the body. Here again, the specific dimensions for the thermal pad are representative and are not limiting for the invention. However, the elongated configuration of the pad is important for reasons noted above.

The thermal pad 14 is also provided with retaining means 64 and 66 which are preferably hook and loop type fasteners available for example under the VELCRO trade name. However, other fasteners may also be employed. The VELCRO type fasteners are particularly desirable since they may be employed in engagement with each other to secure the thermal pad 14 when it is wrapped around a body limb for example. On the other hand, the hook and loop configuration of the VELCRO fasteners also permits them to assist in securing or locating the thermal pad, for example, by engagement with clothing or the like.

The method of use for the portable body having-/cooling apparatus 10 is believed apparent from the preceding description. However, the method of use is briefly described below in order to assure a complete understanding of the invention.

Initially, the reservoir 14 is filled with a suitable fluid, usually hot water or ice water depending upon the particular therapy desired. The thermal pad 12 configured as described above is interconnected with the reservoir by the supply and return tubes 18 and 20 and is then applied to a selected portion of the body to receive hot or cold therapy.

With the thermal pad 12 in place, operation of the pump 24 is initiated by the motor 30 in order to cause hot or cold fluid from the reservoir to circulate through the tubular conduits 54 and 56 on the thermal pad 12 by means of the supply and return tubes 18 and 20. As noted above, this form of circulation of the fluid causes the temperature of the thermal pad 12 to be increased or decreased relatively gradually, at least over a few seconds, in order to minimize thermal shock to the body portion being treated. Fluid is then continually circulated through the conduit means of the thermal pad in order to maintain a generally uniform therapy temperature on the selected body portion. The therapy may be continued for any desired length of time.

Figure 2:
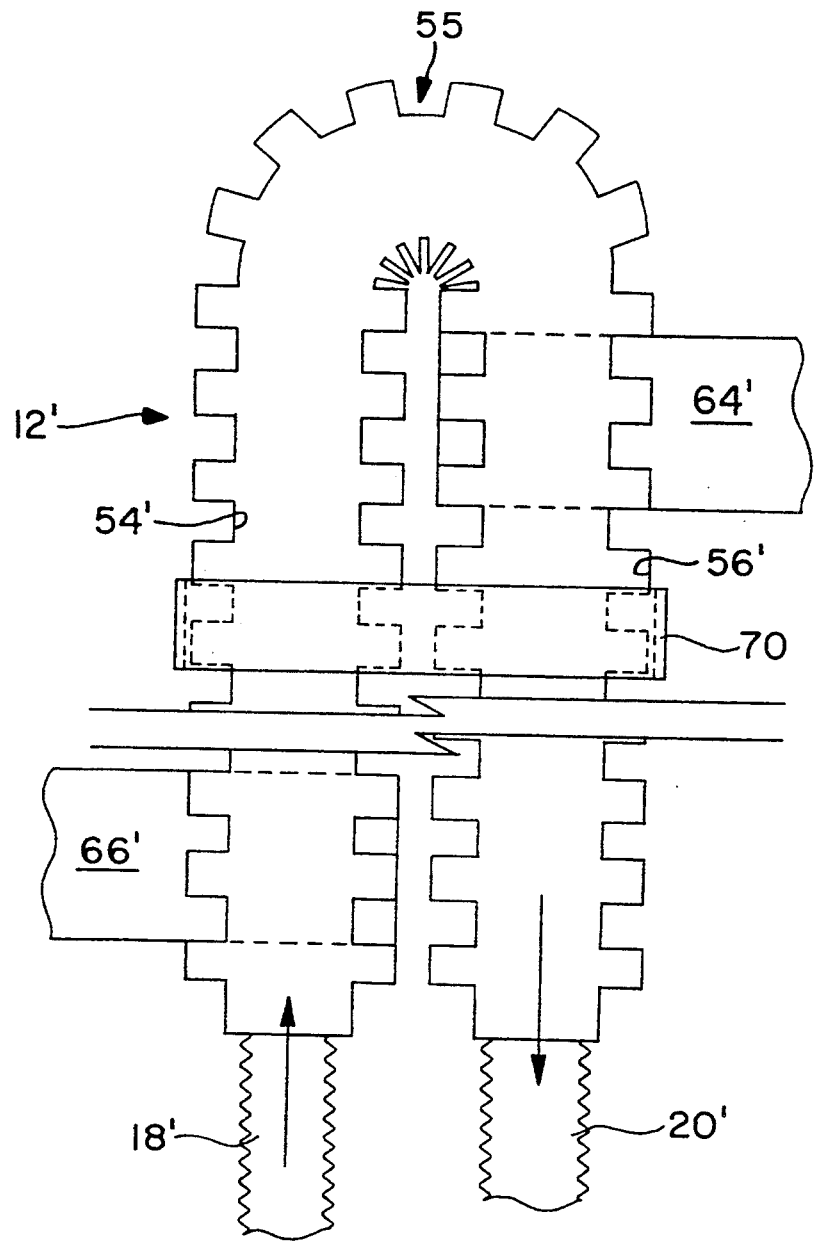
FIG. 2 is a plan view of another embodiment of a thermal pad for use with the heating/cooling system of the invention.

Referring now to FIG. 2, another embodiment of the thermal pad 12 of FIG. 1 is indicated at 12' in FIG. 2. Portions of the thermal pad 12' corresponding to portions of the thermal pad 12 in FIG. 1 are identified by similar primed numerals. In particular, the thermal pad 12' of FIG. 2 is contemplated for use with the same type of reservoir indicated at 14 in FIG. 1.

In particular, the thermal pad 12' is provided with corrugated supply and return tubes 18' and 20' similarly to those described above for the embodiment of FIG. 1. It is again noted that the supply and return tubes 18' and 20' are contemplated for connection with a reservoir such as that indicated at 14 in FIG. 1, the reservoir being deleted from FIG. 2 merely to simplify the drawings and to avoid duplication with FIG. 1.

The thermal pad 12' may also be considered as an applicator to better describe its function of being applied to a selected body portion for treatment.

The thermal pad or applicator 12' of FIG. 2 is formed from corrugated material which is sufficiently flexible to generally conform to the selected body portion being treated. However, at the same time, the corrugated tubing is sufficiently rigid to maintain its corrugated configuration so that it only provides partial contact with the body portion being treated. This is to be distinguished from the generally continuous and intimate contact with the body portion being treated by the thermal pad 12 of FIG. 1. At the same time, the corrugated tubing of the thermal pad or applicator 12' offers a reduced surface area for contact with the body portion being treated, for example an injured muscle. Accordingly, during initial application of the applicator, the change in temperature of the skin occurs more slowly. Accordingly, the person being treated tends to perceive the treatment as being more gradual and with less severe thermal shock. Still further, spaces formed between corrugation of the applicator or thermal pad 12' tend provide a trap for at least a portion of water condensation resulting from ambient humidity. The trapped water tends to be retained between the corrugations as a result of surface tension in a water film formed on the pad 12' by the condensed water.

As illustrated in FIG. 2, the thermal pad 12' is formed by a single corrugated tube which is bent back on itself to form parallel conduit 54' and 56' corresponding to the tubular portion 54 and 56 of FIG. 1. In addition, a curved portion 55 has a radius of approximately 180° to provide an intraconnection between the parallel portions 54' and 56'.

The corrugated tubing in the thermal pad or applicator 12' may have widely varying dimensions and may be formed from a variety of materials. However, it is preferably contemplated that the tubing be formed from a relatively rigid plastic material such as vinyl, polyethylene or polypropolene. However, it is again noted that the invention requires the applicator to be sufficiently flexible as noted above to conform to the body portion being treated. It is also noted above that the tubing for the applicator 12' of FIG. 2 could also be formed from a metal such as stainless steel or the like as long as it meets the other requirements set forth above.

Unlike the continuous rubber tubing in the thermal pad 12 of FIG. 1, the applicator 12' of FIG. 2 limits the area of contact with the body portion being treated to a selected percentage of the overall area for the corrugated tubing pad or applicator 12', typically about 50%, depending upon the thickness of the corrugations and the spacing or pitch between corrugations (assumed to be approximately equal in order to result in the preferred 50% body contact).

The tubing of the applicator 12' of FIG. 2 is also sufficiently rigid so that it is generally self supporting. Thus, the applicator 12' of FIG. 2 does not include a backing pad 52 as described above for the thermal pad 12 of FIG. 1.

Typical dimensions of the corrugated tubing for the applicator 12' of FIG. 2 are described below but, as noted above, are not intended to limit the present invention. The corrugated tubing forming the parallel conduit 54' and 56' as well as the 180° bend 55 may have a total length of from 2 ft. but could also be as long as 4 or 5 ft. in order to provide a greater surface area for the applicator 12'.

With the corrugated tubing being formed from a relatively hard plastic material such as vinyl, the tubing preferably has a wall thickness in the range of from about 0.005 in. to about 0.060 in., preferably about 0.015 in. The height or depth of the corrugations is typically 0.1 in. Both the width and pitch or spacing between the corrugations is typically 0.06 in. The inside diameter of the corrugated tubing may vary from about 0.25 in. to several inches but is preferably about 0.5 in. It is again noted that these dimensions are set forth only by way of example and are not intended to limit the invention.

The tubing for the applicator 12' is maintained in the configuration illustrated in FIG. 2 with the conduit portions 54' and 56' parallel to each other by one or more retainers such as that illustrated at 70. Only one such retainer 70 is illustrated in FIG. 2. However, additional retainers could be provided if desired. Here again, the number of retainers would also depend upon the overall length of the corrugated tubing in the applicator 12'.

The retainer 70 is preferably a continuous band or loop formed from heat-shrinkable elastomer material facilitating its arrangement upon the applicator 12'.

The applicator 12' is also provided with retaining means 64' and 66' similar to the retaining means 64 and 66 of FIG. 1.

Within the apparatus and method of use as described above, numerous modifications are of course obvious. In particular, the dimensions of the thermal pad 12 may be adjusted in order to make it particularly adaptable to different body portions. The reservoir 14 may also be provided for example with an internal heating source (not shown) which could then be employed for continually heating fluid or liquid within the reservoir, particularly when longer term therapy is contemplated. With an internal heating source, the reservoir could also be provided with thermostat means (also not shown) in order to more accurately regulate temperature of the fluid. Other modifications and additions such as those noted above are believed apparent from the description. Accordingly, the scope of the present invention is defined only by the following claims which are further exemplary of the invention.

What is claimed is:

1. A portable body heating/cooling apparatus for thermal treatment of selected body portions such as joints, muscles and the like, comprising
    an insulated reservoir for containing hot/cold fluid,
    a thermal pad substantially formed by corrugated conduit means configured to allow substantially rapid fluid circulation within the entire conduit means,
    non-collapsible supply and return tubes interconnected between the reservoir and the conduit means in the pad, and
    pump means for continually circulating fluid from the reservoir through the conduit means and back to the reservoir,
    said corrugated conduit means comprising parallel portions formed from a thermally conductive material corrugated on both interior and exterior surfaces and forming alternating ridges and valleys on the exterior surface thereof with corresponding valleys and ridges on the interior surface thereof, the material being sufficiently flexible for conforming to the selected body portion and for producing thermal treatment by the flow of fluid past the valleys and ridges of the entire interior conduit surface, the tubular portions being respectively connected to the supply and return tubes and to each other, the entire pad being elongated for application in extended or flat relation to the body or wrapped around a body joint or limb with the conduit means in direct thermally conductive relation with the heated or cooled circulating fluid therein and the selected body portion to be treated, whereby the use of the corrugated conduit means in combination with the pump means provides rapid and direct thermal change transfer from the circulating heated/cooled fluid across the conduit means to the selected body portion in contact therewith.

2. The portable body heating/cooling apparatus of claim 1 wherein the pump means is battery operated and located in the reservoir.

3. The portable body heating/cooling apparatus of claim 1 further comprising retainer means for securing the thermal pad in contact with the selected body portion.

4. The portable body heating/cooling apparatus of claim 2 wherein the supply and return tubes are formed with an accordion-like configuration to assure constant circulation of fluid through the conduit means of the thermal pad.

5. The portable body heating/cooling apparatus of claim 1 wherein the supply and return tubes are formed with an accordion-like configuration to assure constant circulation of fluid through the conduit means of the thermal pad.

6. The portable body heating/cooling apparatus of claim 1 wherein the conduit means are sufficiently rigid to permit bending without collapse, the exterior ridges of the conduit corrugation proportionally limiting total direct surface area contact of the corrugated conduit means with the body portion being treated and the exterior valleys of the conduit corrugation acting to collect and trap water condensation resulting from ambient environmental humidity.

7. In a method employing a portable body heating/cooling system for thermal treatment, the steps comprising
    storing hot/cold fluid in an insulated reservoir,
    arranging a thermal pad in thermally conductive relation with a selected body portion to be treated, wherein the thermal pad is substantially formed by corrugated conduit means configured to allow substantially rapid fluid circulation within the entire conduit means,
    interconnecting the reservoir and the conduit means in the pad by non-collapsible supply and return tubes, and
    continually pumping the fluid in circulation from the reservoir through the conduit means and back to the reservoir in order to assure continual thermal treatment of the selected body portion,
    said conduit means comprising parallel tubular portions formed from a thermally conductive material corrugated on both interior and exterior surfaces and forming alternating ridges and valleys on the exterior surface thereof with corresponding valleys and ridges on the interior surface thereof, the material being sufficiently flexible for conforming to the selected body portion and for producing thermal treatment by the flow of fluid past the valleys and ridges of the entire interior conduit surface, the conduit portions being respectively connected to the supply and return tubes, the entire pad being elongated for application of the pad in extended or flat relation to the body or wrapped around a body joint or limb with the conduit means in direct thermally conductive relation with both the heated or cooled circulating fluid therein and the selected body portion, whereby the use of the corrugated conduit means in combination with the continual pumping of the fluid provides rapid and direct thermal change transfer from the circulating heated/cooled fluid across the conduit means to the selected body portion in contact therewith.

8. The method of claim 7 further comprising retainer means for securing the thermal pad in contact with the selected body portion.

9. The method of claim 8 wherein the supply and return tubes are formed with an accordion-like configuration to assure constant circulation of fluid through the conduit means of the thermal pad.

10. the method of claim 7 wherein the corrugated conduit means are sufficiently rigid to permit bending without collapse, the exterior ridges of the conduit corrugation proportionally limiting total direct surface area contact of the corrugated conduit means with the body portion being treated and the exterior valleys of the conduit corrugation acting to collect and trap water condensation resulting from ambient environmental humidity.

11. The method of claim 7 wherein the supply and return tubes are formed with an accordion-like configuration to assure constant circulation of fluid through the conduit means of the thermal pad.

* * * * *